(12) United States Patent
Duvaux et al.

(10) Patent No.: US 11,725,044 B2
(45) Date of Patent: Aug. 15, 2023

(54) METHOD FOR PRODUCING POLYCLONAL ANTIBODIES WITH IMPROVED COMPLEMENT-DEPENDENT CYTOTOXICITY

(71) Applicant: XENOTHERA, Nantes (FR)

(72) Inventors: Odile Duvaux, Nantes (FR); Jean-Paul Soulillou, Nantes (FR)

(73) Assignee: Xenothera, Nantes (FR)

( * ) Notice: Subject to any disclaimer, the term of this patent is extended or adjusted under 35 U.S.C. 154(b) by 0 days.

(21) Appl. No.: 15/516,742

(22) PCT Filed: Oct. 15, 2015

(86) PCT No.: PCT/EP2015/073892
§ 371 (c)(1),
(2) Date: Apr. 4, 2017

(87) PCT Pub. No.: WO2016/059161
PCT Pub. Date: Apr. 21, 2016

(65) Prior Publication Data
US 2017/0240616 A1     Aug. 24, 2017

(30) Foreign Application Priority Data
Oct. 15, 2014   (EP) ..................... 14306633

(51) Int. Cl.
| | | |
|---|---|---|
| C07K 16/08 | (2006.01) | |
| A01K 67/027 | (2006.01) | |
| C07K 16/06 | (2006.01) | |
| C12P 21/00 | (2006.01) | |
| C07K 16/12 | (2006.01) | |
| C07K 16/10 | (2006.01) | |
| A61K 39/00 | (2006.01) | |
| C12N 9/10 | (2006.01) | |
| C07K 16/44 | (2006.01) | |
| C12N 9/02 | (2006.01) | |

(52) U.S. Cl.
CPC .......... *C07K 16/08* (2013.01); *A01K 67/0276* (2013.01); *C07K 16/06* (2013.01); *C07K 16/10* (2013.01); *C07K 16/12* (2013.01); *C12P 21/005* (2013.01); *C12Y 114/18002* (2013.01); *C12Y 204/01087* (2013.01); *A01K 2217/075* (2013.01); *A01K 2217/15* (2013.01); *A01K 2227/108* (2013.01); *A01K 2267/01* (2013.01); *A01K 2267/02* (2013.01); *A61K 2039/505* (2013.01); *C07K 16/44* (2013.01); *C07K 2317/10* (2013.01); *C07K 2317/20* (2013.01); *C07K 2317/41* (2013.01); *C07K 2317/734* (2013.01); *C12N 9/0071* (2013.01); *C12N 9/1048* (2013.01); *C12N 2760/14111* (2013.01)

(58) Field of Classification Search
CPC ..... C07K 16/08; C07K 16/12; A01K 67/0276
See application file for complete search history.

(56) References Cited

U.S. PATENT DOCUMENTS

| | | | |
|---|---|---|---|
| 9,062,338 B1 * | 6/2015 | Lin ................ | C12Y 114/18002 |
| 9,888,674 B2 * | 2/2018 | Tector ................. | C12N 9/1048 |
| 11,084,871 B2 * | 8/2021 | Soulillou ............... | C07K 16/18 |
| 2006/0216702 A1 * | 9/2006 | Compans ................. | C12N 7/00 |
| | | | 435/235.1 |
| 2010/0150942 A1 | 6/2010 | Cantor | |
| 2010/0196410 A1 * | 8/2010 | Choi .................. | C07K 14/3156 |
| | | | 424/190.1 |
| 2012/0027771 A1 | 2/2012 | Cantor | |

FOREIGN PATENT DOCUMENTS

| | | |
|---|---|---|
| WO | 03097812 | 11/2003 |
| WO | 20070101441 | 9/2007 |
| WO | 2010149355 | 12/2010 |
| WO | 2013003767 | 1/2013 |
| WO | 2014066505 | 5/2014 |
| WO | 2014170867 | 10/2014 |

OTHER PUBLICATIONS

Warfield, K. L., et al., 2003, Ebola virus-like particles protect from letha Ebola virus infection, PNAS 100(26):15889-15894.*
Lutz et al., "Double knockout pigs deficient in N-glycolylneuraminic acid and Galactose [alpha]-1,3-Galactose reduce the humoral barrier to xenotransplantation", XENOTRANSPLANTATION vol. 20, No. 1, Jan. 5, 2013, pp. 27-35.
Vered et al., "Potential impact of the non-human sialic acid N-glycolylneuramic acid on transplant rejection risk", XENOTRANSPLANTATION vol. 18, No. 1, Jan. 1, 2011, pp. 1-5.
Raju et al., "Species-specific variation in glycosylation of IgG: evidence for species-specific sialylation and branch-specific galactosylation and importance for engineering recombinant glycoprotein therapeutics", Glycobiology, vol. 10, No. 5, Jan. 1, 2000, pp. 477-486.
Tangvoranuntakul et al., "Human uptake and incorporation of an immunogenic nonhuman dietary sialic acid", PNAS, vol. 100, No. 21,Oct. 14, 2003, pp. 12045-12050.
A. Osama Gaber et al: Rabbit Antithymocyte Globulin (Thymoglobulin), 2010 ADIS Data Information BV, Drugs 2010: 70 (6), pp. 691-732.
Thea D'Ambrosio: "Office Action Summary", U.S. Appl. No. 14/785,138, dated May 9, 2017.

* cited by examiner

*Primary Examiner* — Jeffrey S Parkin
(74) *Attorney, Agent, or Firm* — WCF IP

(57) ABSTRACT

The present invention relates to polyclonal antibodies directed against at least one non-human biological pathogen, or against at least one molecule derived from said pathogen, towards a human or a non-human animal organism, wherein the said polyclonal antibodies are devoid of an antigenic determinant selected in a group comprising (i) N-glycolneuraminic acid (Neu5Gc) and/or (ii) a-1,3-galactose, and their use as a medicament.

2 Claims, 4 Drawing Sheets

Viral Load in sera at Day 3

* p=0.012

Viral load (EBOLA genome/ml)

Non-immune IgG D0 — Immune IgG D0

Figure 3

METHOD FOR PRODUCING POLYCLONAL ANTIBODIES WITH IMPROVED COMPLEMENT-DEPENDENT CYTOTOXICITY

FIELD OF THE INVENTION

The present invention relates to the field of immunology and more particularly to polyclonal antibodies directed against non-human biological pathogens or molecules derived from said pathogens, towards human or animal organisms, and their use in medicine.

DESCRIPTION OF RELATED ART

Antibodies are "Y" shaped protein molecules that are naturally produced by the body as part of the immune defense. One of the primary roles of antibodies is binding to molecules that are not recognized by the immune system as part of the body. For example, the immune system creates antibodies to bind to pathogens, like bacteria and viruses, to neutralize their effects and to help the immune system clear an infection.

Most antibody therapeutics are monoclonal antibodies. Monoclonal antibodies are antibodies that bind to one epitope. Essentially, they are all the same antibody rather than a collection of different antibodies. Monoclonal antibodies are created by researchers using a variety of known methods.

The choice of polyclonal antibodies over monoclonal antibodies for most antibody therapeutics today makes sense because polyclonal antibodies (pAbs) are antibodies that are secreted by highly diverse B cell and plasmacytes lineages within the body (whereas monoclonal antibodies come from a single cell lineage). Thus, polyclonal hyper immune antibodies are a collection of highly diverse immunoglobulin molecules, of various classes and isotypes that react against a specific antigen, but each identifying a different epitope. On the contrary, associations of monoclonal antibodies are limited to few molecules and cannot mimic the polyclonal diversity of polyclonal antibodies.

In addition, polyclonal antibodies act through a variety of mechanisms (notably complement and cell dependent cytotoxicity (CDC and ADCC), neutralization, opsonisation, etc.) that only a variety of molecular target and Ig classes and isotypes can offer and which cannot be replicated by a monoclonal antibody, or even by associations of monoclonal antibodies. As example, polyclonal IgG against human T cell interact against at least 50 clusters of differentiation (CDs) (Popov et al., Transplantation, 2012).

Hence, usage of passive serotherapy using sera or purified polyclonal immunoglobulins from animals (rabbit, horse, goat) has been a first major advance in treating or preventing the dissemination of severe infectious diseases, such as Plague or Diphtheria.

However, despite demonstrated efficacy, the injection in humans of immune immunoglobulins (IgG or IgM for instance) from animals may remain immunogenic and is responsible for the generation of immune complex related diseases (ICD) and severe unwanted adverse effects, such as serum sickness disease (SSD), including severe forms (with myocarditis, nephropathies for instance) or other immune complex manifestations such as skin rashes, fever, head ache, arthritis or pseudo meningitis syndrome, etc.

Human ICD have been modeled in animal (F Dixon J Exp Med 1956). The most common and well identified complication in humans following injection of animal IgG is the serum sickness disease (SSD), which is observed in almost 100% of young individual presenting a type 1 diabetes and receiving Thymoglobulin, a purified rabbit IgG anti-T lymphocyte preparation, and in the absence of any other immunosuppressive agents (SE Giteman et al., The Lancet Diabetes & Endocrinology, 1:306, 2003).

Beside the safety concerns, passive immunotherapy in most of humans being faces the presence of preexisting anti non-human animal Ig which modify the biodisponibility of the material injected and possibly its early efficacy. Indeed, it is known that most of humans being already have said anti non-human animal Ig due to their diet and their intestinal biotope. Even in case of an efficient preparation of therapeutic non-human animal Ig and intended to be administered in humans, the severe and highly frequent SSD are thus a major safety and possibly efficacy obstacle for passive immunotherapy in non-immunosuppressed recipients with severe infectious diseases. In addition the safety concerns may also restrict a wide utilization of preventive campaign in possibly contaminated persons in the patient's vicinity.

What is more, presence of SSD clinical manifestations is a clinical drawback for correctly assessing the result of a therapeutic or preventive procedure using purified polyclonal antibodies. Indeed, clinical symptoms of SSD include notably head ache, fever, arthritis or pseudo meningitis syndrome, which can all mislead a correct appraisal of disease evolution.

Thus, there remains a need for the provision of therapeutic polyclonal antibodies from non-human mammal(s) capable to efficiently prevent and/or treat disorders due to non-human biological pathogens infections, and having reduced adverse effects, including therapeutic polyclonal antibodies which would be significantly less immunogenic when compared to the conventional polyclonal antibodies and which would be ideally not associated with manifestations of IC related diseases.

SUMMARY OF THE INVENTION

According to a first of its aspects, the invention relates to a polyclonal antibody directed against at least one non-human biological pathogen, or at least one molecule derived from said pathogen, towards a human or a non-human animal organism, preferably towards a human organism, wherein the said polyclonal antibody is devoid of a first antigenic determinant selected in a group comprising (i) N-glycolneuraminic acid (Neu5Gc) and (ii) α-1,3-galactose.

According to another of its aspect, the invention relates to a composition comprising at least polyclonal antibodies such as above-defined.

According to another of its aspects, the invention relates to a method for producing polyclonal antibodies, or a composition comprising polyclonal antibodies, such as above-defined, comprising the steps of:

a) providing a genetically altered non-human mammal lacking a first gene selected in a group comprising (i) a gene encoding a functional cytidine-5'-monophosphate N-acetyl neuraminic acid hydrolase (CMAH) and (ii) a gene encoding a functional α-(1,3)-galactosyltransferase (alpha1,3GT, GGTA1 or GT1);

b) immunizing the said genetically altered non-human mammal against at least one non-human biological pathogen(s), towards a human or a non-human animal organism, preferably towards a human organism, or against at least one molecule(s) derived from said pathogen(s); and c) collecting the antibodies contained in a body fluid of the said genetically altered non-human mammal of step b).

According to a preferred embodiment, the genetically altered non-human mammal lacks only the gene encoding a functional cytidine-5'-monophosphate N-acetyl neuraminic acid hydrolase (CMAH).

According to another preferred embodiment, the genetically altered non-human mammal lacks the two genes selected in the group characterized by (i) the gene encoding a functional cytidine-5'-monophosphate N-acetyl neuraminic acid hydrolase (CMAH) and (ii) the gene encoding a functional α-(1,3)-galactosyltransferase (alpha1,3GT, GGTA1 or GT1).

As it is known in the art, antibodies directed against non-human biological pathogens for human or animal organisms, preferably for human organisms, may be easily obtained by immunizing a non-human mammal, which includes notably pigs, horses or rabbits, by administration of an immunogenic composition comprising target non-human biological pathogens or antigens derived thereof (namely molecules derived from said pathogens), with or without adjuvants.

Then, polyclonal antibodies of any class or isotype against any kind of non-human biological pathogens may be obtained by immunizing a non-human mammal with the said non-human biological pathogens, or alternatively antigens derived thereof (namely molecules derived from said pathogens).

This includes polyclonal antibodies of therapeutic interest, which antibodies are directed against non-human biological pathogens, the presence of which in a human or a non-human animal organism, especially human organism, is undesirable.

This includes polyclonal antibodies directed against microorganisms exerting deleterious effects to the human or a non-human animal organism, especially human organism.

Therefore, the said non-human biological pathogen for a human or an animal organism is preferably selected in a group comprising bacteria, parasites, mushrooms, virus, toxins, venom and a combination thereof. However, the polyclonal antibodies known in the art, especially antibodies generated in animals, notably non-human mammals, such as pigs or rabbits, remain immunogenic in human due to notably of the presence of α-1,3-galactose and/or N-glycolneuraminic acid (Neu5Gc) epitopes on these known polyclonal antibodies, which epitopes are recognized by the cells of the immune system in human.

For overcoming these drawbacks of known polyclonal antibodies, the present invention contemplates the use of a genetically altered non-human mammal lacking a first gene selected from the group comprising (i) a gene encoding a functional cytidine-5'-monophosphate N-acetyl neuraminic acid hydrolase (CMAH) and (ii) a gene encoding a functional α-(1,3)-galactosyltransferase, for producing polyclonal antibodies (or a composition comprising them) directed against at least one non-human biological pathogen for a human or a animal organism, or against at least one molecule derived from said pathogen.

The implementation of a such genetically altered non-human mammal is further advantageous in that said genetically altered non-human mammal only develops minimal amount of anti NeuGc antibodies on unmodified diet. Thus, this exempts of a step of immune-absorption of the serum of said genetically altered non-human mammal before its injection in a human patient.

The usage of a KO animal for at least the GT1 gene has also the advantage to not further enhance the production of anti Gal antibodies which may protect pathogens (Katopodis A G et al., J. Clin. Invest., 2002).

According to another of its aspects, the invention relates to a polyclonal antibody, or a composition comprising them, according to the invention, for its use as a medicament.

The present invention also pertains to a polyclonal antibody or a composition such as described above for its use for preventing and/or treating a severe infection, in particular a severe infection selected in a group comprising Acinetobacter infections, Actinomycosis, African sleeping sickness (African trypanosomiasis), AIDS (Acquired immunodeficiency syndrome), Amebiasis, Anaplasmosis, Anthrax, Arcanobacterium haemolyticum infection, Argentine hemorrhagic fever, Ascariasis, Aspergillosis, Astrovirus infection, Babesiosis, Bacillus cereus infection, Bacterial pneumonia, Bacterial vaginosis (BV), Bacteroides infection, Balantidiasis, Baylisascaris infection, BK virus infection, Black piedra, Blastocystis hominis infection, Blastomycosis, Bolivian hemorrhagic fever, Borrelia infection, Botulism (and Infant botulism), Brazilian hemorrhagic fever, Brucellosis, Bubonic plague, Burkholderia infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, Chikungunya, Chlamydia, Chlamydophila pneumoniae infection (Taiwan acute respiratory agent or TWAR), Cholera, Chromoblastomycosis, Clonorchiasis, Clostridium difficile infection, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), Enterococcus infection, Enterovirus infection (especially Enterovirus 71 (EV71) (Huang et al., Curr. Opin. Virol., 2014, 12; 5: 98-104)), Epidemic typhus, Erythema infectiosum (Fifth disease), Exanthem subitum (Sixth disease), Fasciolopsiasis, Fasciolosis, Fatal familial insomnia (FFI), Filariasis, Food poisoning by Clostridium perfringens, Free-living amebic infection, Fusobacterium infection, Gas gangrene (Clostridial myonecrosis), Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infection, Group B streptococcal infection, Haemophilus influenzae infection, Hand, foot and mouth disease (HFMD), Hantavirus Pulmonary Syndrome (HPS), Heartland virus disease, Helicobacter pylori infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Middle East respiratory syndrome (MERS), Melioidosis (Whitmore's disease), Meningitis, Meningococcal disease, Metagonimiasis, Microsporidiosis, Molluscum contagiosum (MC), Monkeypox, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis* pneumonia (PCP), Pneumonia, Poliomyelitis, *Prevotella* infection, Primary amoebic meningoencephalitis (PAM), Progressive multifocal leukoencephalopathy, Psittacosis, Q fever, Rabies, Rabies, Respiratory syncytial virus infection, Rhinosporidiosis, Rhinovirus infection, Rickettsial infection, Rickettsialpox, Rift Valley fever (RVF), Rocky Mountain spotted fever (RMSF), Rotavirus infection, Rubella, *Salmonellosis*, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Subacute sclerosing panencephalitis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manum (Ringworm of the Hand), Tinea nigra, Tinea pedis (Athlete's foot), Tinea unguium (Onychomycosis), Tinea *versicolor* (*Pityriasis versicolor*), Toxocariasis (Ocular Larva Migrans (OLM)), Toxocariasis (Visceral Larva Migrans (VLM)), Trachoma, Trinochcliasis, Trichinlosis, Trichomoniasis, Trichuriasis (Whipworm infection), Tuberculosis, Tularemia, *Ureaplasma urealyticum* infection, Valley fever, Venezuelan equine encephalitis, Venezuelan hemorrhagic fever, Viral pneumonia, West Nile Fever, White piedra (Tinea blanca), *Yersinia pseudotuberculosis* infection, Yersiniosis, Yellow fever, Zygomycosis or at least one severe infection(s) induced by at least one antibiotic resistant pathogen(s) (D Roux et al., J. Antimicrob. Chemother., 2012; J D Berry et al., New Biotechnology, 2011, 28: 489-501).

Thus, a non-human biological pathogen considered in the present invention and selected in a group comprising bacteria, parasites, mushrooms, virus, toxins, venom and a combination thereof may be more particularly a non-human biological pathogen which leads to at least one severe infection(s) such as above-described.

The present invention further pertains to a polyclonal antibody or a composition such as described above for its use in seroprophylaxis and/or serotherapy.

The present invention further pertains to a polyclonal antibody or a composition such as described above for its use for decreasing and/or suppressing immune complex related diseases (ICD) and severe unwanted adverse effects, such as serum sickness disease (SSD), including severe forms (with myocarditis, nephropathies for instance) or other immune complex manifestations such as skin rashes, fever, head ache, arthritis or pseudo meningitis syndrome, and induced by the administering of antibodies comprising at least one antigenic determinant selected in a group comprising (i) N-glycolneuraminic acid (Neu5Gc) or (ii) α-1,3-galactose, preferably comprising at least both antigenic determinants (i) N-glycolneuraminic acid (Neu5Gc) and (ii) α-1,3-galactose.

BRIEF DESCRIPTION OF THE FIGURES

FIG. 3: Viral load in sera at Day 3. Virus load in sera at day 3 is evaluated on each animal by RTqPCR analysis with primers targeting EBOLA L Polymerase. Virus load of Guinea pigs receiving the anti Ebola Immune IgG from DKO (n=9) compared to Guinea pigs receiving the Non Immune IgG (n=5) is significantly lower (Mann-Whitney, p=0.012). From left to right: EBOLA virus non plus immune IgG D0, EBOLA virus plus immune IgG D0. The viral load (y-axis) is expressed in EBOLA genome/mL. One Guinea pig receiving the Immune IgG has been excluded from the analysis as an outlier (Virus load value for this animal 3.5E7 genome/ml). No animal from the control Mock PBS group showed any viral load in the serum.

DETAILED DESCRIPTION OF THE INVENTION

1. Definitions

Figure 1:
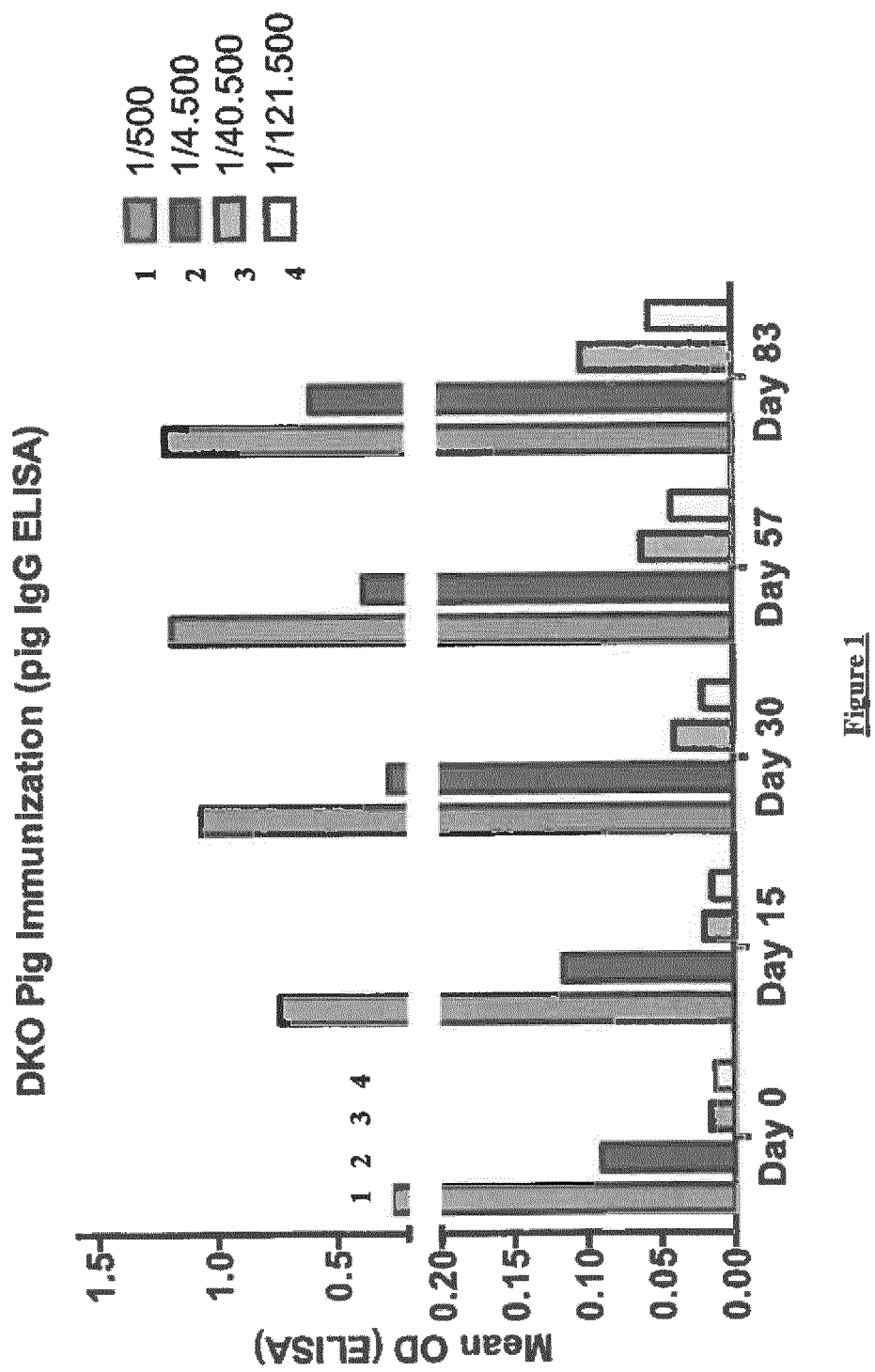
FIG. 1: Double KO Pig Immunization (pig IgG ELISA). One double KO pig has been injected five times with 700 µg of EBOLA GP. Serum samples obtained from immunized double KO pig before immunizations (Day 0), during immunizations (Day 15, Day 30, Day 57) or after immunizations (Day 83) were analyzed for anti-GP specific antibodies by ELISA. Bars represent the mean OD at each time point for each dilution. For each day (0, 15, 30, 57 and 83), from left to right (columns numbered from 1 to 4): serum dilutions at 1/500; 1/4500; 1/40.500; 1/121.500, respectively. Mean Optical Density (OD) is expressed on the y-axis.
Figure 2:
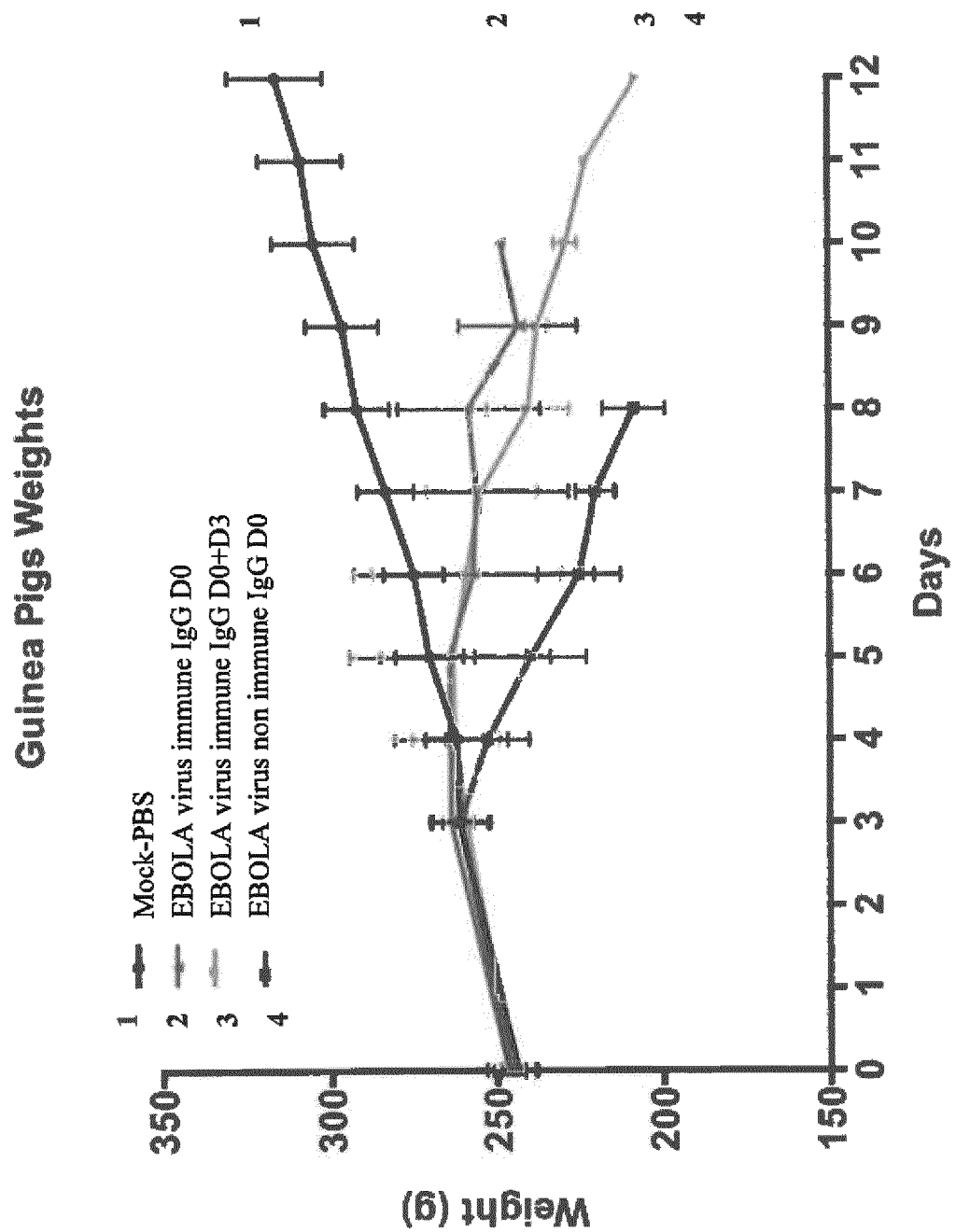
FIG. 2: Guinea Pigs weight variation during experiment. Each number represents one Guinea Pig group. Standard deviation is represented for each group, for each time point: «1» is Mock-PBS. «2» is EBOLA virus plus immune IgG D0 group. «3» is EBOLA virus plus immune IgG D0+D3. «4» is EBOLA virus plus non immune IgG D0. The weight (g) is expressed in the y-axis. Days are expressed on the x-axis.

In order that the invention may be more completely understood, several definitions are set forth below. Such definitions are meant to encompass grammatical equivalents.

As used herein, the term "comprising" encompasses "consisting of".

The term "antibody" is used herein in the broadest sense. "Antibody" refers to any polypeptide which at least comprises (i) a Fc region and (ii) a binding polypeptide domain derived from a variable region of an immunoglobulin. Antibodies thus include, but are not limited to, full-length immunoglobulins, antibodies, antibody conjugates and fragments of each respectively. The terms "antibody" and "immunoglobulin" may be used interchangeably herein.

The term "antibody" encompasses a polypeptide as above-mentioned which further comprises at least one sugar moiety distinct from the antigenic determinant selected in a group comprising (i) N-glycolneuraminic acid (Neu5Gc) and/or (ii) α-1,3-galactose.

By "polyclonal antibodies" as used herein is meant a mixture of antibodies recognizing different epitopes of a given antigen. Polyclonal antibodies encompass those which are contained in, or alternatively which are derived from, body fluids, especially serum or plasma from a non-human mammal organism.

Within the general meaning of the present invention, an antibody according to the invention is directed against at least one non-human biological pathogen, or against at least one molecule derived from said pathogen, for a human or a non-human animal organism.

As used herein, a "natural" or "endogenous" antibody refers to an antibody that is not derived from recombinant DNA.

In the case of human immunoglobulins, light chains are classified as kappa and lambda light chains. Heavy chains are classified as mu, delta, gamma, alpha, or epsilon, and define the antibody's isotype as IgM, IgD, IgG, IgA, and IgE, respectively.

By "IgG" as used herein is meant a polypeptide belonging to the class of antibodies that are substantially encoded by a recognized immunoglobulin gamma gene. In humans, IgG comprises the subclasses or isotypes IgG1, IgG2, IgG3, and IgG4. In mice, IgG comprises IgG1, IgG2a, IgG2b, IgG3. Pigs IgG exhibit 6 different isotypes. In swine, IgG comprises the subclasses or isotypes IgM, IgD, IgG, IgE and IgA antibodies and a large number of IgG subclasses (Butler et al., Developmental and Comparative Immunology 30 (2006) 199-221; Butler et al., Developmental and Comparative Immunology 33 (2009) 321-333). Full-length IgGs consist of two identical pairs of two immunoglobulin chains, each pair having one light and one heavy chain, each light chain comprising immunoglobulin domains VL and CL, and each heavy chain comprising immunoglobulin domains VH, Cγ1 (also called CH1), Cγ2 (also called CH2), and Cγ3 (also called CH3).

As used herein, "Complement Dependent Cytotoxicity" (or CDC) refers to the result of binding of the complement molecules or the diverse pathway of complement activation to complement binding Ig classes and isotypes.

As used herein, "Antibody-dependent cell-mediated toxicity" (or ADCC) refers to a mechanism of cell-mediated immunity whereby an effector cell of the immune system actively lyses a target cell that has been bound by specific antibodies. ADCC is mostly mediated by NK cells but also by other immune cells such as neutrophils and eosinophils. Typically, ADCC results from the activation of NK cells. The activation of NK cells involves the binding of their Fc receptors to the Fc region of IgG bound to antigens present on the surface of target cells. Such interactions induce the release by NK cells of cytokines and cytotoxic granules. To assess the capacity of an antibody to induce ADCC, an assay, as described in de Romeuf et al. Br J Haematol. 2008 March; 140(6):635-43, may be performed.

ADCC and CDC activities may be assessed by well-known methods of the man skilled in the art.

By "antigenic determinant" (or epitope), as applied herein to non-human mammal polyclonal antibodies, as used herein is meant a structural component of an antigenic molecule, which includes an antigenic protein and an antigenic carbohydrate, responsible for its specific interaction with antibody molecules elicited by the same or related antigen. By extension, the term "antigenic determinant", as applied herein to non-human mammal polyclonal antibodies is also used collectively herein for an antigenic molecule comprising a plurality of epitopes, including conformational motives in which the sugar moiety is needed but represent only part of the epitope, susceptible to be recognized by antibody molecules elicited by the same or related antigen. Illustratively, the antigenic molecule N-glycolneuraminic acid (Neu5Gc) may be called herein an "antigenic determinant", although the said antigenic molecule may exhibit more than one epitope recognized by antibodies elicited with Neu5Gc or with Neu5Gc containing molecules.

"T cells" or "T lymphocytes" belong to a group of white blood cells known as lymphocytes, and play a central role in cell-mediated immunity. They can be distinguished from other lymphocytes, such as B cells and natural killer cells (NK cells), by the presence of a T-cell receptor (TCR) on the cell surface. They are called T cells because they mature in the thymus.

"B cells" or "B lymphocytes" also belong to a group of white blood cells known as lymphocytes, making them a vital part of the immune system—specifically the humoral immunity branch of the adaptive immune system. B cells can be distinguished from other lymphocytes, such as T cells and natural killer cells (NK cells), by the presence of a protein on the B cell's outer surface known as a B cell receptor (BCR). This specialized receptor protein allows a B cell to bind to a specific antigen. The main functions of B cells are to make antibodies against antigens, to perform the role of antigen-presenting cells (APCs), and to develop into memory B cells and plasmacytes after activation by antigen interaction.

In blood, the "serum" is the plasma-derived component wherein cells (white blood cells as well as red blood cells) and clotting factors have been removed. Serum includes all proteins not used in blood clotting (coagulation) and all the electrolytes, antibodies, antigens, hormones, and any eventually also exogenous substances (e.g. drugs and microorganisms).

By "conventional polyclonal antibodies", as used herein is meant the polyclonal antibodies that are not devoid of an antigenic determinant selected in a group comprising (i) N-glycolneuraminic acid (Neu5Gc) and (ii) α-1,3-galactose. In this regard, it may be notably cited the products commercialized under the name Thymoglobuline or Veinoglobulin.

The term "pathogen", as used herein, encompasses anything that can produce a disease. The term is herein used to mean an infectious agent which may be selected among the group comprising bacteria, parasites, mushrooms, virus, toxins, venom and a combination thereof, and that causes disease or infection in its host. By extension, the term "pathogen" also encompasses antigenic fractions derived from such an infectious agent (namely any molecules derived from said pathogen), which includes notably antigenic proteins or antigenic polysaccharides thereof.

The term "host", as used herein, encompasses a human organism or a non-human animal organism. It is the reason why a non-human biological pathogen according to the present invention means a pathogen having a noxious effect with respect to a human or a animal organism in good health.

Besides, the term "non-human biological pathogen towards a human or an animal organism", as used herein, encompasses all pathogens of non-human nature which are not naturally present, or which are naturally present but in non-infectious amount, in a human or a animal organism in good health.

This term also encompasses saprophytic organisms which may be pathogenic when the human organism or the non-human animal organism is immunosuppressed.

Preferably, a non-human biological pathogen towards a human or a animal organism is a non-human biological exogenous pathogen towards a human or a animal organism.

The term "molecule derived from a non-human biological pathogen towards a human or an animal organism" as used herein refers broadly to any antigen to which a human or an animal organism can generate an immune response. This "molecule" (or "antigen") as used herein refers broadly to molecule that contains at least one antigenic determinant to which the immune response may be directed. The immune response may be cell mediated or humoral or both. The molecule derived from a non-human biological pathogen may be protein in nature, carbohydrate in nature, lipid in nature, or nucleic acid in nature, or combinations of these biomolecules. The molecule derived from a non-human biological pathogen may also include molecules such as polymers and the like.

The term "nucleic acid", as used herein, encompasses ribonucleic acid (RNA) and deoxyribonucleic acid (DNA), which include nucleic acids selected from the group comprising or consisting of: single-stranded deoxyribonucleotide(s) (ssDNA); double-stranded deoxyribonucleotide(s) (dsDNA); single-stranded ribonucleotide(s) (ssRNA); double-stranded ribonucleotide(s) (dsRNA); single-stranded oligo-deoxyribonucleotide(s) (ssODNA); double-stranded oligo-deoxyribonucleotide(s) (dsODNA); single-stranded oligo-ribonucleotide(s) (ssORNA); double-stranded oligo-ribonucleotide(s) (dsORNA); RNA-DNA duplexes.

In a non-limitative manner, said nucleic acids may be in the form of messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers.

2. Composition According to the Invention

With the view of overcoming the drawbacks of the conventional polyclonal antibodies directed against undesirable pathogens or molecules derived from said pathogens, the inventors have conceived polyclonal antibodies, and compositions comprising them, having reduced immunogenic properties in human individuals and thus having reduced ability to induce severe unwanted adverse effects, especially Immunogenic Complex (IC).

What is more, polyclonal antibodies according to the present invention are further particularly interesting in that they have an increased "Complement Dependent Cytotoxicity" (or CDC) and "Antibody-dependent cell-mediated toxicity" (or ADCC) activity.

This invention primarily relates to a polyclonal antibody directed against at least one non-human biological pathogen, or against at least one molecule derived from said pathogen, towards a human or a non-human animal organism, wherein the said polyclonal antibody is devoid of a first antigenic determinant selected in a group comprising (i) N-glycolneuraminic acid (Neu5Gc) and (ii) α-1,3-galactose.

According to a particular embodiment, a polyclonal antibody according to the present invention may be further devoid of a second antigenic determinant which is distinct from the first antigenic determinant and wherein the said second antigenic determinant is selected in a group comprising (i) N-glycolneuraminic acid (Neu5Gc) and (ii) α-1,3-galactose.

The invention relates in particular to "non human" polyclonal antibodies, such as the ones produced by a genetically altered non-human mammal as herein described.

More specifically, the invention relates to a non-human mammal polyclonal antibody directed against at least one non-human biological pathogen(s), or against at least one molecule(s) derived from said pathogen(s), towards a human or a non-human animal organism, wherein the said polyclonal antibody is devoid of:
   a first antigenic determinant selected in a group consisting of (i) N-glycolneuraminic acid (Neu5Gc) and (ii) α-1,3-galactose; and
   a second antigenic determinant distinct from the first antigenic determinant and selected in a group consisting of (i) N-glycolneuraminic acid (Neu5Gc) and (ii) α-1,3-galactose.

Also, the present invention relates to a composition comprising at least polyclonal antibodies according to the present invention.

The polyclonal antibodies according to the invention, or a composition comprising them, are believed to possess reduced immunogenic properties in human, as compared with the polyclonal antibodies and compositions comprising them that are currently used in the art.

It is known in the art that Neu5Gc is immunogenic in humans (Noguchi A. et al., J. Biochem. Tokyo (1995), 117(1): 59-62; Scobie L et al., J. immunol., 2012). Further, it is known that patients developing severe Immune Complex (IC) following infusion of animals immunoglobulins mount antibodies which are mostly developed against the Neu5Gc epitope (Merrick J M et al., Int. Allergy Appl. Immunol., 1978, Vol. 57: 477-480; Aggarwal S. et al., Nat Biotechnol. 2008; 26:1227-1233; Arnold J N et al., Annu Rev Immunol. 2007; 25:21-50; Durocher Y et al., Curr Opin Biotechnol. 2009; 20:700-707; Higgins E et al., Glycoconj. J. 2009).

It is also known in the art that the enzyme α1,3-galactosyltransferase (α1,3GT or GGTA1) synthesizes α1,3-galactose (α1,3Gal) epitopes (Galα1,3Galβ1,4GlcNAc-R), which are the major xenoantigens causing hyperacute rejection in pig-to-human xenotransplantation.

Consequently, polyclonal antibodies, and mechanically a composition containing them, devoid of (i) N-glycolneuraminic acid (Neu5Gc) and/or (ii) α-1,3-galactose antigenic determinants, because these polyclonal antibodies are less immunogenic than conventional polyclonal antibodies, possesses reduced immunogenic. Then, such polyclonal antibodies according to the invention, and a composition containing them, are believed to possess reduced properties in raising the various adverse effects that are induced after administration of conventional polyclonal antibodies products, which include immune complex related diseases (ICD) and severe unwanted adverse effects, such as serum sickness disease (SSD), including severe forms (with myocarditis, nephropathies for instance) or other immune complex manifestations such as skin rashes, fever, head ache, arthritis or pseudo meningitis syndrome, etc.

Thus, polyclonal antibodies according to the invention, and a composition containing them, are believed to reduce the risk of occurrence of the conventional polyclonal antibodies-induced adverse effects, as well as their severity if they still occur, as shown herein.

What is more, polyclonal antibodies according to the invention, and a composition containing them, are believed to display an increased "Complement Dependent Cytotoxicity" (or CDC) and "Antibody-dependent cell-mediated toxicity" (or ADCC) activity.

According to the inventors knowledge, no polyclonal antibodies devoid of an antigenic determinant selected in a group comprising (i) Neu5Gc and/or (ii) α-1,3-galactose for the use disclosed in the present specification is known in the art.

In this regard, polyclonal antibodies according to the invention, and a composition containing them, are particularly advantageous in that they precisely allow overcoming or decreasing the above-mentioned undesirable effects caused by the conventional polyclonal antibodies in that they preserve their immune-modulating properties while being less toxic at a systemic level of the human or animal organism, preferably of the human organism.

In other words, polyclonal antibodies according to the invention, and a composition containing them, are significantly less immunogenic and thus, the occurrence of undesirable effects, especially immune complex (IC) related diseases, observed with conventional polyclonal antibodies is expected to be significantly reduced. This beneficial effect due to a lower immunogenicity of the polyclonal antibodies of the invention is particularly relevant when these polyclonal antibodies are injected into normal individuals, namely individuals with an efficient immune response, as in the case of a preventive medical indication such as in a prophylaxis treatment (prevention) in the vicinity of an infected patient.

In addition, it is known in the art that N-glycosylation of antibodies plays a crucial role in the modulation of their effectors properties, especially of their pro- or anti-inflammatory properties.

Thus, it has been identified that the sialylation is the addition of N-acetylneuraminic acid, also called Neu5Ac, NANA, N-acetylsialic or sialic acid, on galactose residues of N-glycans of the crystallizable fragment (Fc) of antibodies.

The sialylation imparts to antibodies particularly interesting anti-inflammatory properties (Dimitrov et al.; Nephrol. Dial. Transplant., 2007.22: 1301 and WO 2007/117505).

Therefore, according to the embodiment wherein polyclonal antibodies according to the present invention are devoid of at least the antigenic determinant N-glycolneuraminic acid (Neu5Gc), said polyclonal antibodies are further advantageous in that they display, by allowing a more physiological access to Fc Gamma receptor, an increased affinity for FcγR.

Therefore, polyclonal antibodies according to this embodiment display an increased "Complement Dependent Cytotoxicity" (or CDC) and "Antibody-dependent cell-mediated toxicity" (or ADCC) activity with respect to considered non-human biological pathogen.

In addition, due to the absence, in polyclonal antibodies according to the present invention, of the antigenic determinant selected in a group comprising (i) N-glycolneuraminic acid (Neu5Gc) and/or (ii) α-1,3-galactose, said polyclonal antibodies, when administered to a human organism, do not raise an immune response including production of anti-Neu5Gc or anti-GAL antibodies, which antibodies contributing to the occurrence of undesirable effects, especially the occurrence of immune complex related diseases (ICD) and severe unwanted adverse effects, such as serum sickness disease (SSD), including severe forms (with myocarditis, nephropathies for instance) or other immune complex manifestations such as skin rashes, fever, head ache, arthritis or pseudo meningitis syndrome, etc.

A method intended to identify or characterize polyclonal antibodies according to the present invention falls within the general knowledge of a man skilled in the art.

A method that may be used by the one skilled in the art for identifying or characterizing polyclonal antibodies according to the invention includes an Enzyme-linked immuno sorbent assay (ELISA) wherein anti-Neu5Gc antibodies and/or anti-Gal antibodies are used as detection molecules. Lectins which are specific for Neu5Gc or 1-3 Gal can also be cited (such as for example IB4 for 1,3 GAL); These lectins are well known by the man skilled in the art.

As anti-Neu5Gc antibodies for assessing the lack of Neu5Gc antigenic determinant, it may be cited the use of chicken IgY anti-Neu5Gc or lectins and the Gc-Free Basic Kit commercialized by the company Sialix, Inc.

As anti-Gal antibodies to demonstrate the lack of α-1,3-galactose antigenic determinant, may be considered the protocol disclosed in Jianq-Qiang Wang et al. (J. Am. Chem. Soc., 1999, 121: 8181) or those commercialized under the name WH0051083M1 Sigma by the company Sigma-Aldrich.

According to an ELISA method wherein specific anti-Neu5Gc and/or anti-Gal antibodies, or lectins, would be immobilized in wells of a microtiter plate, sole the antibodies which comprise the antigenic determinant selected in a group comprising (i) N-glycolneuraminic acid (Neu5Gc) and/or (ii) α-1,3-galactose form a complex with the said anti-Neu5Gc and/or anti-Gal antibodies and thus, remain bound to the wells. When using such an ELISA method, polyclonal antibodies according to the invention are those which are devoid of one or more of the antigenic determinants selected in a group comprising (i) N-glycolneuraminic acid (Neu5Gc) and/or (ii) α-1,3-galactose, and are consequently those which do not form complexes with (i) anti-Neu5Gc antibodies, (ii) anti-Gal antibodies or (iii) both anti-Neu5Gc antibodies and anti-Gal antibodies.

Alternatively, the polyclonal antibodies according to the invention to be studied can be first bound the plate and the identifying reagents can be utilized thereafter. As identifying reagents, may be cited lectins which are specific for Neu5Gc or 1,3 Gal or anti-Neu5Gc antibodies and/or anti-Gal antibodies.

The present invention also relates to a method for producing polyclonal antibodies, or a composition, according to the present invention and such as defined above, comprising the steps of:

a) providing a genetically altered non-human mammal lacking a first gene selected in a group comprising (i) a gene encoding a functional cytidine-5'-monophosphate N-acetyl neuraminic acid hydrolase (CMAH) and (ii) a gene encoding a functional α-(1,3)-galactosyltransferase;

b) immunizing the said genetically altered non-human mammal against at least one non-human biological pathogen(s) towards a human or a non-human animal organism, or against at least one molecule(s) derived from said pathogen(s); and c) collecting the antibodies contained in a body fluid of the said genetically altered non-human mammal of step b).

Preferably, the step b) is carried out by implementation of at least one molecule derived from at least one specific non-human biological pathogen towards a human or a non-human animal organism.

In some embodiments, the composition according to the invention may be prepared by mixing the polyclonal antibodies collected at step c) of the method described above, with one or more adjuvants and/or one or more pharmaceutically acceptable excipients, such as a physiologically acceptable carrier, excipients or stabilizers.

In some embodiments, the polyclonal antibodies are purified before being used in a composition according to the invention.

In some embodiments, a composition of polyclonal antibodies according to the invention is in liquid form.

In some of the embodiments, a composition of polyclonal antibodies according to the invention is in a solid form, which includes a lyophilized form.

The composition of the invention may be formulated according to standard methods such as those described in Remington: The Science and Practice of Pharmacy (Lippincott Williams & Wilkins; Twenty first Edition, 2005).

A composition of the invention may further comprise at least one adjuvant, one pharmaceutically acceptable excipient, or a mixture thereof.

As used herein, the term "adjuvant" refers to its ordinary meaning of any substance that enhances the immune response to an antigen with which it is mixed. Adjuvants useful in the present invention include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (*Bacillus* Calmette-Guerin) and *Corynebacterium parvum*.

Any adjuvant known in the art may be used in a composition according to the present invention, including oil-based adjuvants such as Freund's Complete Adjuvant and Freund's Incomplete Adjuvant, mycolate-based adjuvants (e.g., trehalose dimycolate), bacterial lipopolysaccharide (LPS), peptidoglycans (i.e., mureins, mucopeptides, or glycoproteins such as N-Opaca, muramyl dipeptide [MDP], or MDP analogs), proteoglycans (e.g., extracted from *Klebsiella pneumoniae*), streptococcal preparations (e.g., OK432), Biostim™ (e.g., 01 K2), the "Iscoms" of EP 109 942, EP 180 564 and EP 231 039, aluminum hydroxide, saponin, DEAE-dextran, neutral oils (such as miglyol), vegetable oils (such as arachid oil), liposomes, Pluronic® polyols, the Ribi adjuvant system (see, for example GB-A-2 189 141), or interleukins, particularly those that stimulate cell mediated immunity. An alternative adjuvant consisting of extracts of Amycolata, a bacterial genus in the order Actinomycetales, has been described in U.S. Pat. No. 4,877,612. Additionally, proprietary adjuvant mixtures are commercially available. The adjuvant used will depend, in part, on the recipient organism. The amount of adjuvant to administer will depend on the type and size of animal. Optimal dosages may be readily determined by routine methods.

Suitable adjuvants include but are not limited to surfactants, e.g., hexadecylamine, octadecylamine, lysolecithin, dimethyldioctadecylammonium bromide, N,N-dioctadecyl-N'-N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof. Other potential adjuvants include the B peptide subunits of *E. coli* heat labile toxin or of the cholera toxin. Mc Ghee, J. R. et al., "On vaccine development" Sem. Hematol., 30:3-15 (1993).

The adjuvant properties of saponin have been long known, as has its ability to increase antibody titers to immunogens. As used herein, the term "saponin" refers to a group of surface-active glycosides of plant origin composed of a hydrophilic region (usually several sugar chains) in association with a hydrophobic region of either steroid or triterpenoid structure. Although saponin is available from a number of diverse sources, saponins with useful adjuvant activity have been derived from the South American tree *Quillaja saponaria* (Molina). Saponin from this source was used to isolate a "homogeneous" fraction denoted "Quil A" (Dalsgaard, K., (1974), Arch. Gesamte Virusforsch. 44:243).

In certain embodiments of a composition according to the invention, said composition may further comprises, as pharmaceutical excipients, one or more charged inorganic carriers. Examples of suitable charged organic carriers include, but are not limited to, saponin, saponin complexes, any one or more components of the immunostimulating complex of saponin, cholesterol and lipid known as ISCOMATRIX™ (for example the saponin component and/or the phospholipid component), liposomes or oil-in-water emulsions. (The composition and preparation of ISCOMATRIX™ is described in detail in PCT/SE86/00480, Australian Patent Numbers 558258 and 632067 and EP 0 180 564, the disclosures of which are incorporated herein by reference).

Further adjuvants may be those that are described in the book of Vogel et al. (Vogel F. R., Powell M. F. and Alving C. R., "A compendium of vaccine adjuvants and excipients"; 2<nd> Edition; Vogel F. R. and Powell M F, 1995, "A summary compendium of vaccine adjuvants and excipients. In: Powell M F, Newman M J eds. "Vaccine design: the subunit and adjuvant approach". New York: Plenum publishing, 1995: 141-228).

Pharmaceutically acceptable excipients that may be used are, in particular, described in the Handbook of Pharmaceuticals Excipients, American Pharmaceutical Association (Pharmaceutical Press; 6th revised edition, 2009).

In order to treat a patient in need, such as above-mentioned, a therapeutically effective dose of polyclonal antibodies according to the invention, or a composition comprising them, may be administered.

By "therapeutically effective dose" herein is meant a dose that produces the effects for which it is administered. The exact dose will depend on, notably, the purpose of the treatment, the nature of the disease/infection, the degree of severity of the disease/infection, and will be ascertainable by one skilled in the art using known techniques.

Dosages may range from 0.001 to 100 mg or more of polyclonal antibodies according to the invention per kg of body weight (mg/kg) or greater, for example 0.1, 1.0, 10, or 50 mg/kg of body weight, with 1 to 10 mg/kg being preferred. The dosage and frequency of administration may be adapted depending of the nature of the disease/infection, the degree of severity of the disease/infection, the host response as well as the frequency of injection owing to a better tolerance. Dosage and schedule may be different for treatment and prophylaxis usages.

Also, any injection may be followed by any usual procedure to prevent and/or avoid anaphylactic reaction.

Besides, the injection of polyclonal antibodies according to the invention or of a composition comprising them can be performed through a large peripheral access or, if possible, through a central catheter.

As is known in the art, adjustments for protein degradation, systemic versus localized delivery, as well as the age, body weight, general health, sex, diet, time of administration, possible allergy, drug interaction and the severity of the condition may be necessary, and is easily determined with routine experimentation by those skilled in the art.

Administration of the composition of the invention may be done in a variety of ways, including, but not limited to, orally, subcutaneously, intravenously, parenterally, intranasally, intraortically, intraocularly, rectally, vaginally, transdermally, topically (e.g., gels), intraperitoneally, intramuscularly, intrapulmonary or intrathecally.

Administration of the composition of the invention may be done by following the Besredka method.

The composition of the invention may be administered with other therapeutics concomitantly, i.e., the therapeutics described herein may be co-administered with other therapies or therapeutics, including for example, small molecules, other biologicals, radiation therapy, surgery, etc.

In a most preferred embodiment, a composition according to the invention is in a form suitable for administration by intravenous route.

According to a particular embodiment, a composition according to the invention may further comprise at least one anti-inflammatory drug, such as glucocorticoids.

3. Method for Producing Polyclonal Antibodies (and a Composition Comprising them) According to the Invention As above-mentioned, a method for producing polyclonal antibodies, or a composition comprising them, according to the present invention and such as defined above, comprises the steps of:
   a) providing a genetically altered non-human mammal lacking a first gene selected in a group comprising (i) a gene encoding a functional cytidine-5'-monophosphate N-acetyl neuraminic acid hydrolase (CMAH) and (ii) a gene encoding a functional $\alpha$-(1,3)-galactosyltransferase;
   b) immunizing the said genetically altered non-human mammal against at least one non-human biological pathogen(s) towards a human or a non-human animal organism, or against at least one molecule(s) derived from said pathogen(s); and
   c) collecting the antibodies contained in a body fluid of the said genetically altered non-human mammal of step b).

According to a particular embodiment, the genetically altered non-human mammal may further lacks a second gene distinct from the first gene, the said second gene being selected from the group comprising (i) a gene encoding a functional cytidine-5'-monophosphate N-acetyl neuraminic acid hydrolase (CMAH) and (ii) a gene encoding a functional $\alpha$-(1,3)-galactosyltransferase.

Thus the invention relates more specifically to a method for producing polyclonal antibodies, or a composition comprising them, according to the present invention and such as defined above, comprising the steps of:
   a) providing a genetically altered non-human mammal lacking:
   a first gene selected in a group consisting of (i) a gene encoding a functional cytidine-5'-monophosphate N-acetylneuraminic acid hydrolase (CMAH) and (ii) a gene encoding a functional $\alpha$-(1,3)-galactosyltransferase; and
   a second gene distinct from the first gene, the said second gene being selected from the group consisting of (i) a gene encoding a functional cytidine-5'-monophosphate N-acetyl neuraminic acid hydrolase (CMAH) and (ii) a gene encoding a functional $\alpha$-(1,3)-galactosyltransferase;
   b) immunizing the said genetically altered non-human mammal against at least one non-human biological pathogen(s) towards a human or a non-human animal organism, or against at least one molecule(s) derived from said pathogen(s); and
   c) collecting the antibodies contained in a body fluid of the said genetically altered non-human mammal of step b).

Preferably, the method of the invention may further comprises a step d) of purifying the said polyclonal antibodies, or a specific class or a specific isotype of said polyclonal antibodies, from the said body fluid.

A polyclonal antibody of the invention, when produced by a genetically altered non-human mammal as herein described can also be referred as a "non-human mammal" polyclonal antibody.

Accordingly, a polyclonal antibody according to the present invention, when produced by a genetically altered non-human mammal as herein described may be a natural/endogenous non-human polyclonal antibody.

Alternatively, the polyclonal antibody (i.e. an IgG), when produced by a genetically altered non-human mammal (i.e. a bovine) as herein described and further expressing exogenous immunoglobulin genes (i.e. human immunoglobulin genes), may be a non-natural non-human polyclonal antibody.

3.1. Step a) of Providing a Genetically Altered Non-Human Mammal

For preparing polyclonal antibodies according to the invention, it is performed a first step a) consisting of providing a genetically altered non-human transgenic mammal lacking a gene selected in a group comprising (i) a gene encoding a functional cytidine-5'-monophosphate N-acetyl neuraminic acid hydrolase (CMAH) and/or (ii) a gene encoding a functional $\alpha$-(1,3)-galactosyltransferase.

Preferably, the said genetically altered non-human mammal is a CMAH and/or GGTA1 knockout non-human transgenic mammal (or CMAH and/or GGTA1 KO non-human mammal), which includes a CMAH and GGTA1 double-knockout non-human transgenic mammal.

As used herein, a "knockout (KO) non-human transgenic mammal" consists of a non-human transgenic mammal in which the function of one or more alleles of the considered gene has been altered, for example, by homologous recombination or other insertion or deletion.

In certain embodiments, this gene is disrupted. By "disrupted gene" is meant a portion of the genetic code has been altered, thereby affecting transcription and/or translation of that segment of the genetic code, e.g., rendering that segment of the code unreadable through knockout techniques or by insertion of an additional gene for a desired protein or insertion of a regulatory sequence that modulates transcription of an existing sequence.

In some embodiments of the invention, all of the cells of the non-human transgenic mammal include the disrupted gene.

In certain embodiments, the knockout non-human transgenic mammal is a non-human transgenic mammal in which one or more alleles of the considered gene has been rendered nonfunctional.

In some embodiments, both alleles of the considered gene are rendered non-functional. Such embodiments include those commonly referred to as "gene knockouts", "gene knock-ins" and any other modification of one or more native allele of the native considered gene that renders such gene non-functional. Such non-human transgenic mammal is useful as the source for producing a composition according to the present invention.

A method for obtaining a genetically altered non-human mammal lacking a gene selected in a group comprising (i) a gene encoding a functional cytidine-5'-monophosphate N-acetyl neuraminic acid hydrolase and/or (ii) a gene encoding a functional α-(1,3)-galactosyltransferase falls within the general knowledge of a man skilled in the art.

A genetically altered non-human mammal lacking the gene encoding a functional cytidine-5'-monophosphate N-acetyl neuraminic acid hydrolase is called CMAH KO non-human mammal.

A genetically altered non-human mammal lacking the gene encoding a functional α-(1,3)-galactosyltransferase is called GAL KO non-human mammal.

A method for obtaining a CMAH knockout non-human transgenic mammal is notably described in WO 2006/133356 which more particularly discloses a method for producing animal products devoid of N-glycomeuraminic acid (Neu5Gc) for human use comprising the steps of: preparing a genetically altered non-human mammal lacking a functional cytidine-5'-monophosphate N-acetyl neuraminic acid hydrolase (CMAH) gene; and extracting at least one animal product from the genetically altered non-human animal.

A method for obtaining a GAL knockout non-human transgenic mammal falls within the general knowledge of the man skilled in the art (Cooper D K et al., Genetically engineered pigs, Lancet 1993, 342: 682; Lai L et al., Science 2002, 295: 1089; Sachs D H et al., Current Opinion in Organ Transplantation, 2009, 14:148-153).

A method for obtaining a GAL knockout non-human transgenic mammal is notably described in U.S. Pat. No. 7,547,816.

According to a particular embodiment, to obtain polyclonal antibodies according to the present invention, and a composition comprising them, that is to said polyclonal antibodies directed against non-human biological pathogen, or against at least one molecule derived from said pathogen, towards a human or a non-human animal organism, wherein the said polyclonal antibodies are devoid of an antigenic determinant selected in a group comprising (i) N-glycolneuraminic acid (Neu5Gc) and (ii) α-1,3-galactose, involves the implementation of a genetically altered non-human mammal lacking a gene selected in a group comprising (i) a gene encoding a functional cytidine-5'-monophosphate N-acetyl neuraminic acid hydrolase (CMAH) and (ii) a gene encoding a functional α-(1,3)-galactosyltransferase.

In other words, said specific genetically altered non-human mammal is a double CMAH and GAL knockout (KO) non-human transgenic mammal.

A protocol to obtain this specific CMAH and GAL double knockout non-human transgenic mammal is described in Lutz A L et al. (Xenotransplantation, 2013; 20 (1): 27-35) or in Conchon S. et al. (Xenotransplantation; special issue International Xenotransplantation Association IXA 2013, 2013, Vol. 20, Issue 5).

As genetically altered non-human transgenic mammal which may be used in the present invention, may be notably cited Ovidae, Bovidae, Suidae, Leporidae and Equidae.

Preferably, the genetically altered non-human transgenic mammal may consist of a mouse, a rat, a guinea pig, a rabbit, a goat, a sheep, a llama, a pig, preferably of a pig.

Indeed, pigs are preferred for obtaining polyclonal antibodies according to the present invention in that they are particularly interesting on an industrial point of view.

Indeed, pigs offer several advantages, notably compared to the rabbit, in that the volume of immune sera, and thus of polyclonal antibodies of interest, which may be collected is proportional to the animal's weight ratio (30 times better).

What is more, pigs do not need to be euthanized at sera harvesting time and thus, legal procedures allowing harvesting sera are significantly facilitated.

Indeed, 10% of animal blood volume per month may be collected.

For all these reasons, to obtain a composition according to the present invention from a genetically altered transgenic pig is particularly economic.

3.2. Step b) of Immunizing the Genetically Altered Non-Human Mammal Against Non-Human Biological Pathogen Towards a Human or a Non-Human Animal Organism Once a genetically altered non-human transgenic mammal lacking a gene selected in a group comprising (i) a gene encoding a functional cytidine-5'-monophosphate N-acetyl neuraminic acid hydrolase (CMAH) and/or (ii) a gene encoding a functional α-(1,3)-galactosyltransferase is obtained, a solution comprising notably at least one non-human biological pathogen(s), or at least one molecule(s) derived from said pathogen(s), against which a protection for a human or a non-human animal organism is researched, is then injected.

Preferably, a non-human biological pathogen(s) of step b) may be selected among bacteria, parasites, mushrooms, virus, toxins, venom and a combination thereof, or at least one molecule(s) derived from said pathogen(s), and more particularly among those inducing at least one of the specific severe infections hereinafter described.

For example, a method for obtaining a solution comprising notably a specific non-human biological pathogen, or at least one molecule(s) derived from said pathogen, with respect to a specific related disease/infection falls within the general knowledge of a man skilled in the art.

Preferably, the pathogenic power of the considered non-human biological pathogen is attenuated.

For example, in an embodiment wherein the non-human biological pathogen is a virus, it is preferably the attenuated (or killed) virus or only an extract of this virus which is injected to the above-described genetically altered non-human transgenic mammal.

A method for obtaining an attenuated pathogen, especially an attenuated virus, falls within the general knowledge of a man skilled in the art.

In other words, methods for obtaining a molecule derived from a specific non-human biological pathogen towards a human or a non-human animal organism fall within the general knowledge of a man skilled in the art.

In this regard, it may be cited the use of virus culture supernatants, of recombinant viruses, of lysates of cells transfected or transduced with a virus or a component thereof. Besides, in the case of a toxin, it may be inactivated chemically or with heat (this toxin rendered harmless is frequently called a "toxoid").

A protocol to obtain a good level of immunization of the non-human transgenic mammal with respect to T cells, but also applicable by analogy with respect to a specific non-human biological pathogen towards a human or a non-human animal organism, or a molecule derived from said pathogen, is notably described in EP 0 335 804.

A such protocol may notably consists to immunize animals, such as rabbits, horses or pigs, preferably pigs, with repeated administration, according to known methods, of at least one specific non-human biological pathogen(s), preferably a unique specific non-human biological pathogen, or of at least one molecule(s) derived from said pathogen(s), towards human or animal organisms, and preferably towards human organisms.

For example, several administrations are performed, intravenously or subcutaneously. Preferably, the first administration is subcutaneously, with or without adjuvant, and the other administration is intravenously, of $10^6$ to $10^9$ cells each time, the administrations being spaced of at least a week. About two weeks after the last immunization, serum is collected from immunized animals and isolated according to known methods.

The genetically altered non-human transgenic mammal will produce antibodies against the specific non-human biological pathogen, or the molecule(s) derived from said pathogen, said specific antibodies being devoid of the antigenic determinant Neu5Gc and/or α-1,3-Gal according to the nature of the considered genetically altered non-human transgenic mammal.

3.3. Step c) of Collecting the Antibodies Contained in the Body Fluid of the Genetically Altered Non-Human Mammal of Step b).

Then, a portion of the blood fluid of said genetically altered non-human transgenic mammal is removed from which antibodies, whose antibodies of interest, are collected.

According to a particular embodiment, the said body fluid may be selected in a group comprising blood plasma and blood serum.

A protocol for obtaining a blood fluid, and more particularly a blood plasma or a blood serum, falls within the general knowledge of a man skilled in the art.

3.4. Optional Step d) of Purifying the Antibodies from the Body Fluid of Step c)

According to a preferred embodiment, and as above-mentioned, a method according to the invention may further comprise a step d) of purifying the antibodies from the said body fluid.

Said step d) of purifying is advantageous in that it notably allows overcoming possible unwanted side effects associated with the presence, within the body fluid, of various cellular contaminants which may involve, by the immunized non-human mammal, to the formation of corresponding contaminating antibodies.

Said step d) of purifying is also advantageous in that it allows obtaining composition having a desired degree of purity.

Said step d) of purifying falls within the general knowledge of a man skilled in the art. All possible adaptation of any conventional purifying protocol also falls within the general knowledge of a man skilled in the art.

As an appropriate method for obtaining polyclonal antibodies according to the present invention, may notably be cited the method of fractionated precipitation with ethanol, with ammonium sulfate, with rivanol, with polyethylene glycol or with caprylic acid, the method by passage through ion exchange columns; other methods can involve affinity columns on protein A or G. The antibodies obtained can be then subjected to conventional treatments for their intravenous administration, for example by enzymatic cleavage treatments plasmin, papain or pepsin.

In this regard, may be more particularly cited the protocol implemented in example 3 of EP 0 335 804, which implements an ion exchange chromatography on DEAE cellulose.

According to other embodiments, polyclonal antibodies according to the present invention, and also a composition according to the invention, may consist of polyclonal antibodies and of a composition wherein the antibodies obtained at step c) of the method described above are separated from other cellular substituents other than antibodies, including notably neutrophils, monocytes, red blood cells and platelets.

According to these other embodiments, polyclonal antibodies according to the invention, and also a composition according to the invention, may consist of purified polyclonal antibodies and of a composition containing the purified polyclonal antibodies that are initially present in the serum, the said purified polyclonal antibodies being substantially free of protein components of the serum or even polyclonal antibodies that are substantially free of any substance that was initially contained in the serum used as the starting product.

As an appropriate method for purifying these polyclonal antibodies of interest, may be cited those methods for purifying antibodies with an affinity support onto which coupled to the antigen, on protein G or on protein A, for example those commercialized by the companies Proteo-Genix, Cell Biolabs, Inc. or CliniSciences or still disclosed in EP 1 601 697, JP 7 155 194 or U.S. Pat. No. 6,870,034.

May also be cited the immune affinity purification of polyclonal antibodies specific for at least one particular pathogen or for at least one component of it.

The purification can also concern a specific class or a specific isotype of polyclonal antibodies according to the present invention.

May also be cited an affinity support for the selective fixation of the polyclonal antibodies of interest from a blood fluid, comprising a solid support material having immobilized aptamer which specifically binds said antibodies of interest from a blood fluid. Such a method is notably disclosed in WO 2010/094901.

Alternatively to the use of polyclonal antibodies obtained from a genetically altered non-human mammal, as above-described, the present invention also encompasses polyclonal antibodies obtained after immunizing a wild non-human mammal against at least one non-human biological pathogen(s), or at least one molecule(s) derived from said pathogen(s).

The term "wild non-human mammal" comes herein in opposition with a genetically altered non-human mammal. In other words, by "wild non-human mammal", is meant a non-human mammal which is not lacking at least one gene selected in a group comprising (i) a gene encoding a functional cytidine-5'-monophosphate N-acetyl neuraminic acid hydrolase (CMAH) and/or (ii) a gene encoding a functional α-(1,3)-galactosyltransferase.

In this regard, and so as to remain in the aims of the present invention, the polyclonal antibodies obtained from such a wild non-human mammal have to be then desilylated by appropriate biochemical (especially enzymatic) treatment(s).

In other words, polyclonal antibodies according to the present invention may be obtained (1) from a genetically altered non-human mammal such as above-described or (2) from biochemical (especially enzymatic) treatment(s) of polyclonal antibodies obtained from a wild non-human mammal which has been immunized against at least one non-human biological pathogen(s) towards a human or a non-human animal organism, or against at least one molecule(s) derived from said pathogen(s).

4. Medical Uses According to the Invention

As above-mentioned, the present invention, according to one of its aspects, relates to the use of a genetically altered non-human mammal lacking a first gene selected from the group comprising (i) a gene encoding a functional cytidine-5'-monophosphate N-acetyl neuraminic acid hydrolase (CMAH) and (ii) a gene encoding a functional α-(1,3)-galactosyltransferase, for producing a composition comprising polyclonal antibodies directed against at least one non-human biological pathogen, or against at least one molecule derived from said pathogen, towards a human or a non-human animal organism, preferably towards a human organism.

According to a particular embodiment, this genetically altered non-human mammal may be further lacking a second gene distinct from the first gene, the said second gene being selected from the group comprising (i) a gene encoding a functional cytidine-5'-monophosphate N-acetyl neuraminic acid hydrolase (CMAH) and (ii) a gene encoding a functional α-(1,3)-galactosyltransferase.

More specifically, the invention relates to a use of a genetically altered non-human mammal lacking:

a first gene selected from the group consisting of (i) a gene encoding a functional cytidine-5'-monophosphate N-acetyl neuraminic acid hydrolase (CMAH) and (ii) a gene encoding a functional α-(1,3)-galactosyltransferase; and a second gene distinct from the first gene, the said second gene being selected from the group consisting of (i) a gene encoding a functional cytidine-5'-monophosphate N-acetyl neuraminic acid hydrolase (CMAH) and (ii) a gene encoding a functional α-(1,3)-galactosyltransferase;

for producing polyclonal antibodies, or compositions comprising them, according to the invention and such as defined above.

In particular, the absence of anti-Neu5Gc antibodies in a sample may be assessed according to the dosage method described in Padler-Karavani V et al. (PLoS One. 2013; 8 (3): e58443).

According to another particular embodiment, a composition of the present invention may be a serum directed against at least one non-human biological pathogen, or against at least one molecule derived from said pathogen, towards a human or a non-human animal organism, preferably towards a human organism.

This invention also relates to a polyclonal antibody or a composition comprising them as described throughout the present specification, for its use as a medicament.

Accordingly, and in view of the above, it is understood that the invention also relates to a polyclonal antibody, or a composition comprising them, according to the invention, for its use for the preparation of a medicament.

The present invention pertains to a polyclonal antibody or a composition comprising them as described throughout the present specification, for its use for preventing and/or treating a severe infection.

Hereinafter is displayed a list of non-exhaustive severe infections, namely *Acinetobacter* infections, Actinomycosis, African sleeping sickness (African trypanosomiasis), AIDS (Acquired immunodeficiency syndrome), Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis (BV), *Bacteroides* infection, Balantidiasis, *Baylisascaris* infection, BK virus infection, Black piedra, *Blastocystis hominis* infection, Blastomycosis, Bolivian hemorrhagic fever, *Borrelia* infection, Botulism (and Infant botulism), Brazilian hemorrhagic fever, Brucellosis, Bubonic plague, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, Chikungunya, *Chlamydia*, *Chlamydophila pneumoniae* infection (Taiwan acute respiratory agent or TWAR), Cholera, Chromoblastomycosis, Clonorchiasis, *Clostridium difficile* infection, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection (especially Enterovirus 71 (EV71)), Epidemic typhus, Erythema infectiosum (Fifth disease), Exanthem subitum (Sixth disease), Fasciolopsiasis, Fasciolosis, Fatal familial insomnia (FFI), Filariasis, Food poisoning by *Clostridium perfringens*, Free-living amebic infection, *Fusobacterium* infection, Gas gangrene (Clostridial myonecrosis), Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome (HPS), Heartland virus disease, *Helicobacter pylori* infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human *ewingii* ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Middle East respiratory syndrome (MERS), Melioidosis (Whitmore's disease), Meningitis, Meningococcal disease, Metagonimiasis, Microsporidiosis, Molluscum contagiosum (MC), Monkeypox, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis* pneumonia (PCP), Pneumonia, Poliomyelitis, *Prevotella* infection, Primary amoebic meningoencephalitis (PAM), Progressive multifocal leukoencephalopathy, Psittacosis, Q fever, Rabies, Rabies, Respiratory syncytial virus infection, Rhinosporidiosis, Rhinovirus infection, Rickettsial infection, Rickettsialpox, Rift Valley fever (RVF), Rocky Mountain spotted fever (RMSF), Rotavirus infection, Rubella, *Salmonellosis*, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Subacute sclerosing panencephalitis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manum (Ringworm of the Hand), Tinea nigra, Tinea pedis (Athlete's foot), Tinea unguium (Onychomycosis), Tinea versicolor (Pityriasis versicolor), Toxocariasis (Ocular Larva Migrans (OLM)), Toxocariasis (Visceral Larva Migrans (VLM)), Trachoma, Trinochccliasis, Trichinlosis, Trichomoniasis, Trichuriasis (Whipworm infection), Tuberculosis, Tularemia, Ureaplasma urealyticum infection, Valley fever, Venezuelan equine encephalitis, Venezuelan hemorrhagic fever, Viral pneumonia, West Nile Fever, White piedra (Tinea blanca), Yersinia pseudotuberculosis infection, Yersiniosis, Yellow fever, Zygomycosis or severe infection(s) induced by at least one antibiotic resistant pathogen(s).

Accordingly, the present invention pertains to a polyclonal antibody or a composition comprising them as described throughout the present specification, for its use for preventing and/or treating Ebola hemorrhagic fever.

The present invention also concerns a polyclonal antibody or a composition comprising them as described throughout the present specification, for its use in seroprophylaxis and/or serotherapy.

The term "seroprophylaxis" as used herein relates to the injection of an immune serum obtained from an immunized animal, preferably an immunized non-human mammal, for the purpose of preventing at least one infectious disease(s) in human or a non-human animal organism, preferably in human, said infectious disease(s) being consecutive to at least one non-human biological pathogen.

The term "serotherapy" as used herein relates to the injection of an immune serum obtained from an immunized animal, preferably an immunized non-human mammal, for the purpose of treating at least one infectious disease(s) in human or a non-human animal organism, preferably in human, said infectious disease(s) being consecutive to at least one non-human biological pathogen.

Accordingly, the present invention pertains to a polyclonal antibody or a composition comprising them as described throughout the present specification, for its use for preventing and/or treating a severe infection by a pathogen selected from a group consisting of toxins, venom and combinations thereof.

Said toxins and venoms may be selected from the group comprising or consisting of: botulinum toxin, tetanus toxin, Shiga toxin, Diphtheria toxin, Pertussis toxin, neurotoxins, myotoxins, hemotoxins, cytotoxines, toxins of plant origin, mycotoxins, taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin, ricin, CC-1065, toxins derived from poisonous animals, and animal venoms; and analogs or homologs thereof.

Examples of animal venoms include snake venom, spider venom, bee venom, fish venom, jellyfish venom, scorpion venom, snail venom; including viper venom, cobra venom, crotalid venom, Naja venom; and analogs or homologs thereof.

The present invention also concerns a polyclonal antibody or a composition comprising them as described throughout the present specification, for its use for decreasing and/or suppressing immune complex related diseases (ICD) and severe unwanted adverse effects, such as serum sickness disease (SSD), including severe forms (with myocarditis, nephropathies for instance) or other immune complex manifestations such as skin rashes, fever, head ache, arthritis or pseudo meningitis syndrome, and induced by the administering of antibodies comprising at least one antigenic determinant selected in a group comprising (i) N-glycolneuraminic acid (Neu5Gc) or (ii) α-1,3-galactose, preferably comprising at least both antigenic determinants (i) N-glycolneuraminic acid (Neu5Gc) and (ii) α-1,3-galactose.

EXAMPLE

In all herein after examples, the implemented pigs all have an unmodified diet.

Example 1: Protocol for Preparing Polyclonal Antibodies Against Ebola Hemorrhagic Fever Virus from a Double GAL/CMAH KO Pig Preliminarily, the implemented double GAL/CMAH KO pig is the one disclosed in Lutz A L et al. (Xenotransplantation, 2013; 20 (1): 27-35) or the one disclosed in Conchon S. et al. (Xenotransplantation; special issue International Xenotransplantation Association IXA 2013, 2013, Vol. 20, Issue 5).

1) Protocol of Immunization of the Double GAL/CMAH KO Pig with Respect to the Ebola Hemorrhagic Fever Virus Immunization of the double GAL/CMAH KO pig described in Lutz A L et al. (Xenotransplantation, 2013; 20 (1): 27-35) or in Conchon S. et al. (Xenotransplantation; special issue International Xenotransplantation Association IXA 2013, 2013, Vol. 20, Issue 5) is carried out by administration of soluble forms of Ebola virus glycoproteins (GP) released into the culture medium from cells expressing these proteins (as disclosed in Live attenuated recombinant vaccine protects nonhuman primates against Ebola and Marburg viruses, Nature Medicine, 2005, Jones, S M et al, or Foreign glycoproteins expressed from recombinant vesicular stomatitis viruses are incorporated efficiently into virus particles, PNAS, 1996, Schnell M J et al or A Marzi, PLoS ONE, 7:e36192).

Accordingly, the immunization can be carried out by administration of 700 µg of Ebola virus glycoproteins.

In this example, the virus antigenic preparation is most preferably Neu5Gc free. The virus antigenic preparation (also called polyclonal hyper-immune sera) fulfills all legal recommendations, at the level of antigen preparation, of the double KO (CMAH and GT1) animal utilized for the immunization and of the good practice manufacturing of all the steps mentioned here below:

a) Performing a first subcutaneous injection of a solution comprising the above-mentioned soluble forms of Ebola virus glycoproteins with aluminum hydroxide as adjuvant followed by two or more intravenous injections (i.e. on days 14 and 21).

b) Optionally, administering intravenously 10 doses of BCG, or any type of adjuvant, at $10^7$-$10^8$ germs/10 doses at day 5.

c) Collecting the serum on day 35 or after, by bleeding. Collecting about 100 ml of pig serum.

Assays (Elisa using Ebola GP for coating of Elisa plates and neutralization test of Ebola GP transfected VSV infectivity for Vero cells) are performed on the serum and reveal titers of 1/10000 and 1/100 respectively.

Accordingly, the immunization can be carried out by performing a first subcutaneous injection of a solution comprising the above-mentioned soluble forms of Ebola virus glycoproteins with aluminum hydroxide as adjuvant followed by four intravenous injections on days 14 and 29, 44, and 78.

Accordingly, the serum can be collected 40 days after the last boost, by bleeding.

2) Protocol for Obtaining Polyclonal (IgG) Antibodies with Respect to the Administered Ebola Hemorrhagic Fever Virus from the Double GAL/CMAH KO Pig A protocol for obtaining polyclonal antibodies (i.e. IgG, IgM, etc.), as herein described is provided, which comprises the following steps:

a) Subjecting the above-mentioned pig serum to a chromatography on Whatman cellulose DEAE and then performing an elution step with a disodium phosphate buffer 1.5 g/L, pH 8.

b) Purifying the obtained gamma-globulin solution by double precipitation with sodium sulphate at 180 g/L, then 170 g/L, pH 7. Re-dissolving the precipitate in a solution of 0.3 M glycine, pH 7, so as to obtain a volume equal to the starting volume.

Alternatively, the above-mentioned step of purification may be carried out using Protein A, preceded by a phase of precipitation with caprylic acid. The purification step may then be followed by ions exchange column. This alternative purification process offered good polyclonal IgG yield of 51% with a purity of 95%.

c) Hema-adsorbing the solution twice on pellets of human red blood cells (volume of pellet for each adsorption substantially equal to the volume of crude serum) to reduce the rate of haemaglutinins. Precipitating again the solution with sodium sulfate to remove hemoglobin. Dissolving the precipitate in 0.3 M glycine buffer, diafiltered against a final solution of glycine 10 g/L, NaCl 2 g/L, mannitol 10 g/L. Adding proteins to 5 g/L, and then lyophilized.

Measuring the Elisa titers of double KO pig anti Ebola GP and of neutralizing anti Ebola virus antibodies (as outlined above) and preventing death of guinea pigs infected with 1,000 $LD_{50}$ of guinea pig-adapted recombinant EBOV. FIG. 1B.

Female guinea pigs (Hartley strain), approximately 200 g (Charles River), will be divided into 4 groups. Of note, the product to inject has been pre-tested in two groups of 5 mice injected IP: one group at 200 microg×4 days and the second at 2 mg×4 days, without apparent toxicity.

Each group comprises FIVE guinea pigs as described below:

| Groups | Protocol |
|---|---|
| Mock-PBS (n = 5) | No EBOLA virus injection<br>PBS injection at D 0 in one leg<br>PBS injection at D 3 in the other leg |
| EBOLA virus-Non Immune IgG D 0 (n = 5) | EBOLA virus injection at D 0 (1000 TCID50)<br>Non Immunized DKO Pig injection at D 0 in two legs (65 mg total) |
| EBOLA virus-Immune IgG D 0 (n = 5) | EBOLA virus injection at D 0 (1000 TCID50)<br>Immunized DKO Pig IgG anti-EBOV.GP injection at D 0 in one leg (68 mg) |
| EBOLA virus-Immune IgG D 0 + D 3 (n = 5) | EBOLA virus injection at D 0 (1000 TCID50)<br>Immunized DKO Pig IgG anti-EBOV.GP injection at D 0 in one leg (68 mg)<br>Immunized DKO Pig IgG anti-EBOV.GP injection at D 3 in the other leg (34 mg) |

Clinical signs of infection and body weight have been monitored for two weeks after challenge. A blood sample has been harvested on day 3 (1 ml if possible) for measuring the virus load and pig IgG concentration. The survivors have been followed up to 15 day post infection. At the end of experiment, or at day of animals death (if applicable), blood samples and organs (spleen, liver, etc) are analyzed.

Comments:

The results provide evidence (see FIG. 3) that animals belonging to the EBOLA virus-Immune IgG D0 group (see above) exhibit statistically significant lower Day 3 virus replication (Viral Load), when compared to animals belonging to the Mock or non-immune IgG group.

Figure 4:
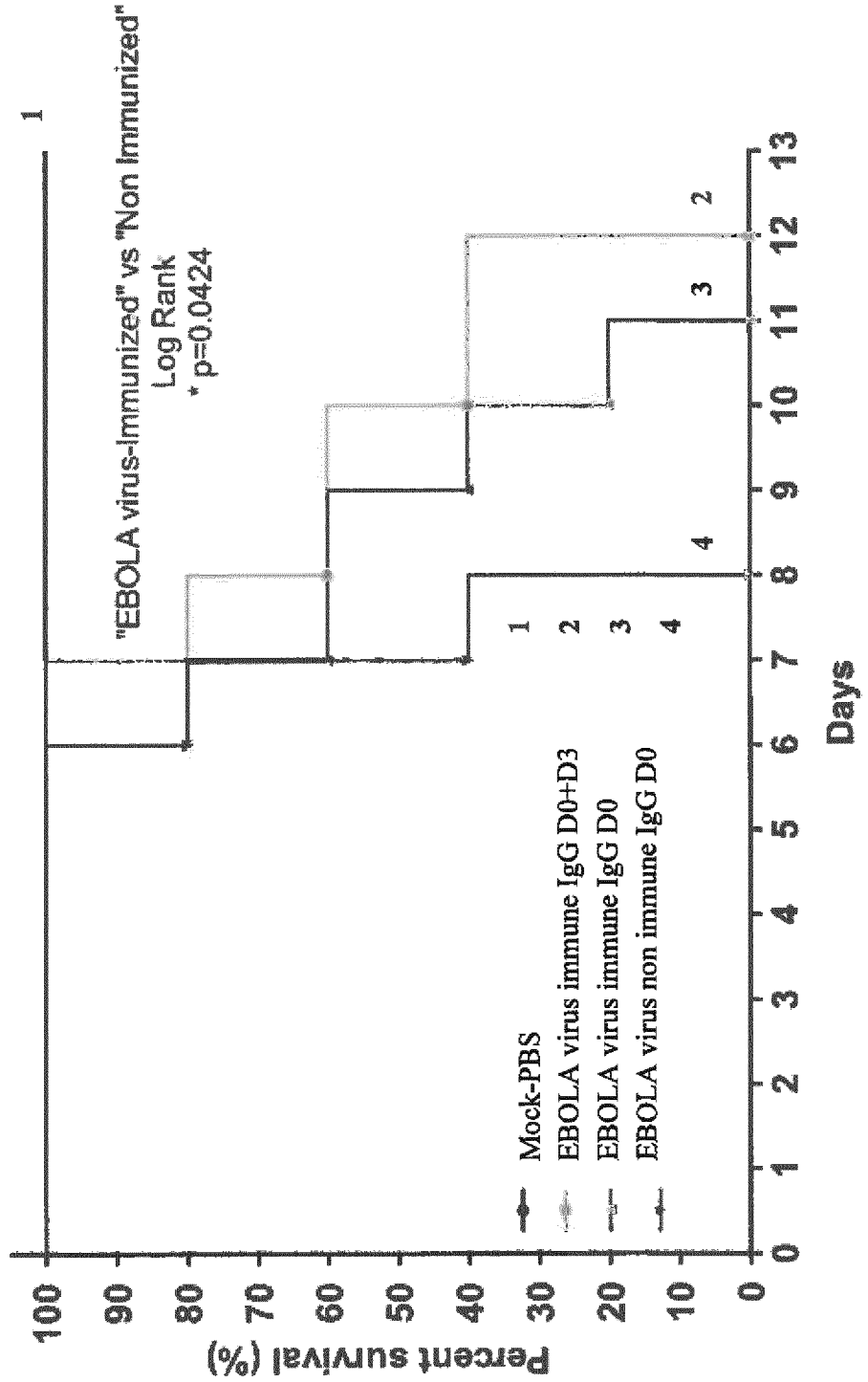
FIG. 4: Kaplan Meier survival curves. Kaplan Meier survival curves indicate the percentage of surviving Guinea pigs at each day of the 12 days post EBOLA virus exposure observation period. Survival of Guinea pigs receiving the anti Ebola immune IgG from DKO pigs (n=10) compared to Guinea pigs receiving the Non immune IgG (n=5) is significantly higher (Log Rank, p=0.0424*). The y-axis indicates percent survival (%). The days are expressed on the x-axis. Each curve is indicated by its corresponding number: Mock-PBS is «1»; «EBOLA virus-plus immune IgG D0+D3» is «2»; «EBOLA virus plus immune IgG D0» is «3»; «EBOLA virus plus non immune IgG D0» is «4».

The results also provide evidence (see FIG. 4) that animals belonging to the EBOLA virus-Immune group survive longer than animals belonging to the EBOLA virus-Non Immune IgG D0 group.

The obtained polyclonal antibodies with respect to the considered non-human biological pathogen (i.e. Ebola hemorrhagic fever virus) from the double GAL/CMAH KO pig is particularly interesting in that they are significantly less immunogenic in humans and more cytotoxic (notably in terms of CDC) compared to conventional polyclonal antibodies with respect to the same considered non-human biological pathogen.

These polyclonal antibodies thus allow efficiently treating or preventing the disease/infection due to the Ebola hemorrhagic fever virus and reducing in parallel the unwanted side effects such as immune complex (IC) related diseases and/or serum sickness that patients may develop consecutively to an injection of conventional polyclonal antibodies. What is more, it is observed that these polyclonal antibodies display a very significant and interesting activity with respect to the Ebola hemorrhagic fever virus due to an increased ADCC and CDC.

All these advantages necessarily improve the well-being of the patient, what is more where the disorder/infection to treat already involves severe symptoms.

Example 2: Measure of Anti-Neu5Gc Antibodies (or Anti-Neu5Gc IgGs) in Double GAL/CMAH KO Pigs Anti-Neu5Gc antibodies in immunized pig serum of example 1 (sampled at day 35 of the immunization protocol) were quantified using an ELISA assay adapted from Scobie et al., J. Immunol., 2013, modified to improve specificity. Briefly, plates were coated with wild-type mouse serum (containing Neu5Gc) overnight at 4° C., then were blocked using PBS 1% ovalbumine 0.05% Tween for 2 hours at room temperature. During this time, samples were pre-incubated for 2 hours on ice with serum from CMAH-KO mice (no expression of Neu5Gc), and with or without 5 mM of synthetic Neu5Gc (for competitive absorption of anti-Neu5Gc antibodies). Samples were then added to the ELISA plate for 2 hours at room temperature. A horseradish peroxidase-labeled goat anti-pig IgG (Fc) secondary antibody (AbD Serotec, reference: AAI41P) was used for detection of anti-Neu5Gc antibodies, and plates were revealed using TMB substrate (Sigma-Aldrich). Optical density was read on a MRX plate reader (Dynatech Laboratories). Results are presented as the difference between the optical density of the wells inhibited or not inhibited by synthetic Neu5Gc.

RESULTS

Thus, double GAL/CMAH KO pigs only develop minimal amount of anti NeuGc antibodies, which shows that there will be no need for immune serum absorption.

The invention claimed is:

1. A method for producing polyclonal antibodies, comprising the steps of:
    a) providing a genetically altered pig lacking:
        (i) a gene encoding a functional cytidine-5'-monophosphate N-acetyl neuraminic acid hydrolase (CMAH) and (ii) a gene encoding a functional α-(1,3)-galactosyltransferase;
    b) immunizing said genetically altered pig against at least one non human biological pathogen(s) towards a human, or against at least one peptidoglycan derived from said pathogen(s); and
    c) collecting the antibodies having improved Complement Dependent Cytotoxicity (CDC) activity contained in a body fluid of said genetically altered pig of step b),
    said biological pathogen, or the peptidoglycan derived from said pathogen, towards a human, being a bacteria or a virus,
    wherein the polyclonal antibodies having an improved CDC activity, as compared to:
    polyclonal antibodies obtained from the same method from a wildtype pig, wherein said wildtype pig comprises (i) a gene encoding a functional cytidine-5'-monophosphate N-acetyl neuraminic acid hydrolase (CMAH) and (ii) a gene encoding a functional α-(1,3)-galactosyltransferase (WT CMAH$^+$/GGTA1$^+$ pig), and
    polyclonal antibodies obtained through the same method from a pig which comprises only one among (i) a gene encoding a functional cytidine-5'-monophosphate N-acetyl neuraminic acid hydrolase (CMAH) (CMAH$^-$/GGTA1$^+$ pig) or (ii) a gene encoding a functional α-(1,3)-galactosyltransferase (CMAH$^+$/GGTA1$^-$ pig).

2. The method according to claim 1, wherein the body fluid is selected from the group consisting of blood plasma and blood serum.

* * * * *